(12) United States Patent
Modi et al.

(10) Patent No.: US 9,575,000 B2
(45) Date of Patent: Feb. 21, 2017

(54) DROP DETECTION OF HUMAN FOLLICLE FLUID IN A TEST TUBE

(71) Applicant: Shivani Scientific Industries Private Limited, Mumbai (IN)

(72) Inventors: Ashish Modi, Mumbai (IN); Ravikant Kale, Mumbai (IN)

(73) Assignee: SHIVANI SCIENTIFIC INDUSTRIES PRIVATE LIMITED, Mumbai (IN)

( * ) Notice: Subject to any disclaimer, the term of this patent is extended or adjusted under 35 U.S.C. 154(b) by 79 days.

(21) Appl. No.: 14/602,091

(22) Filed: Jan. 21, 2015

(65) Prior Publication Data
US 2015/0201967 A1 Jul. 23, 2015

(30) Foreign Application Priority Data

Jan. 22, 2014 (IN) ............................ 233/MUM/2014

(51) Int. Cl.
*G01N 21/59* (2006.01)
*G01N 21/85* (2006.01)

(52) U.S. Cl.
CPC .............. *G01N 21/59* (2013.01); *G01N 21/85* (2013.01); *G01N 2021/8564* (2013.01)

(58) Field of Classification Search
CPC .............. A61B 17/435; A61B 17/3478; A61B 2017/00973; A61B 2034/258; A61B 10/0283; A61B 10/0291; A61M 1/0031; A61M 2210/1441; A61M 2205/502
USPC ................. 600/33–35; 128/897–899
See application file for complete search history.

(56) References Cited

U.S. PATENT DOCUMENTS

| | | | | |
|---|---|---|---|---|
| 4,321,461 A | * | 3/1982 | Walter, Jr. ........... | A61M 5/1689 222/59 |
| 4,824,434 A | * | 4/1989 | Seitz, Jr. ............... | A61B 17/435 600/33 |
| 5,062,304 A | * | 11/1991 | Van Buskirk ...... | A61B 5/14507 4/114.1 |
| 5,346,466 A | | 9/1994 | Yerlikaya et al. | |
| 5,704,923 A | * | 1/1998 | Chiu-Hsiung ...... | G01F 23/2921 604/260 |
| 6,019,735 A | * | 2/2000 | Kensey ............ | A61B 5/150786 600/573 |

(Continued)

FOREIGN PATENT DOCUMENTS

| | | |
|---|---|---|
| CN | 103157155 A | 6/2013 |
| EP | 0622195 B1 | 6/1998 |

*Primary Examiner* — Navin Natnithithadha
*Assistant Examiner* — Sunita Reddy
(74) *Attorney, Agent, or Firm* — Ditthavong & Steiner, P.C.

(57) ABSTRACT

The present disclosure discloses an apparatus and a method for detecting first and subsequent drops of follicle fluid falling into a test tube during an aspiration process. A pair of optical devices (emitter and detector) is positioned at opposite side of the test tube. The emitter emits a beam of light towards the detector. As soon as a drop of the follicle fluid falls into the test tube, a signal processing circuitry detects a change in intensity of the light received by the detector. Further, the intensity of beam is compared with a pre-defined intensity. Based on the comparison, if the difference between the pre-defined intensity and intensity is greater than a pre-defined threshold value, the signal processing circuitry generates an electrical signal indicating the detection of the first drop of the follicle fluid falling into the test tube.

6 Claims, 6 Drawing Sheets

(56) References Cited

U.S. PATENT DOCUMENTS

| | | | |
|---|---|---|---|
| 8,137,967 B2* | 3/2012 | Seidel | A01N 1/02 435/2 |
| 9,134,736 B2* | 9/2015 | Lowery | G05D 7/0635 |
| 2005/0171491 A1* | 8/2005 | Minh Miner | A61M 5/1411 604/257 |
| 2008/0097144 A1* | 4/2008 | Cecchi | A61B 17/435 600/33 |
| 2010/0082011 A1* | 4/2010 | Lewis | A61M 5/14232 604/503 |
| 2011/0160651 A1* | 6/2011 | Lee | A61M 5/16886 604/65 |
| 2012/0116245 A1* | 5/2012 | Steiner | A61B 1/00068 600/563 |
| 2014/0038283 A1* | 2/2014 | Jose | C12M 47/02 435/325 |

* cited by examiner

DROP DETECTION OF HUMAN FOLLICLE FLUID IN A TEST TUBE

CROSS-REFERENCE TO RELATED APPLICATIONS AND PRIORITY

The present application claims priority to Indian Provisional Patent Application No. 233/MUM/2014, filed on Jan. 22, 2014, the entirety of which is hereby incorporated by reference

TECHNICAL FIELD

The present disclosure described herein, in general, relates to detection of drop of a human follicle fluid falling into test tube.

BACKGROUND

In medical science field, one of the treatments for infertility is 'IVF' (In Vitro Fertilization, universally known as the Test Tube Baby). As part of the treatment procedure, it is required that an oocyte (egg) is extracted from female patient in an operation theatre with the female patient under anesthesia.

In the present day situation, an Ultrasound Oocyte Recovery procedure is performed for extracting oocyte from the ovaries within a female patient. In the said procedure, a vaginal ultrasound probe with an attached needle guide is passed into the female's vagina under sterile conditions and the needle is passed through the top of the vagina into the ovary. The follicles are then aspirated until the oocyte is obtained. For aspiration, a vacuum is applied to the end of the test tube tubing end.

In a typical situation, a doctor who is performing the oocyte recovery procedure has his/her both hands occupied in holding the ultrasound probe and the attached needle. He/she may be constantly observing the ultrasound monitor to help him/her guide the needle tip to reach the correct spot in the ovary where the oocyte can be reached and aspirated. To start the aspiration procedure, a foot pedal is pressed. Along with the follicle fluid the oocyte flows inside the needle. At certain stage of the oocyte recovery procedure, the outflow of the follicle fluid may collapse the follicle and at this point the foot pedal has to be released to neutralize the vacuum on the needle tip.

In certain situations it may happen that the passage within the needle or the tubing leading to the test tube gets blocked by a tissue fragment. At this stage the needle has to be extracted out of the patient and a higher level of vacuum may be applied to the set-up. The higher level of vacuum applied may help to remove the blockage in the pathway.

The drops of follicle fluid falling into a test tube directly indicate that there is no blockage in the needle or the tubing. In the situation where there is blockage, very few or no drops may be seen falling into the test tube. In present day situation, a constant watch on the droplets falling is maintained by a person assisting the doctor. The assistant may orally communicate with the doctor, constantly. Droplets falling are expected to begin the moment the doctor presses the foot switch and further the droplets stop falling the moment when the foot switch is released.

Since this droplet status is relayed by the assisting person, delay in communication and loss in continuity may occur. It is required that the doctor gets a uninterrupted and accurate status information of the drops falling into the test tube so that the doctor's vision is dedicated to the ultrasound screen at the time of the operation.

SUMMARY

This summary is provided to introduce aspects related to detection of drop, hereinafter, also referred as droplet or droplets, of a follicle fluid falling into a test tube during recovery of the follicle fluid from patient's body. This summary is not intended to identify essential features of disclosure nor is it intended for use in determining or limiting the scope of the disclosure.

According to various aspects of present disclosure, an apparatus (a drop detector) and a method using the drop detector for detecting the droplets of the follicle fluid in the test tube is disclosed. The purpose of the drop detector is to detect first and subsequent drops of the follicle fluid and ensure the timely retrieval of the follicle fluid in the test tube. Further, the detection of the first and the subsequent drops of the follicle fluid also enable the doctor to ensure that needle is positioned into the patient's body at a correct location. Also, the detection of the drops ensures that there is no blockage in the path and the needle location is still held in a correct position.

Although the purpose and functioning of the drop detector described herein is by taking the follicle fluid as an example, but the drop detector can also be used for other human body fluids as well. Since the follicle fluid is collected in the test tube in a drop-wise manner, it is required to detect the first and the subsequent drops of the follicle fluid coming into the test tube. Upon detecting the first drop, an alert may be generated as an audio/visual signal. The alert generated may indicate the user about the collection of the follicle fluid into the test tube.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to refer to like features and components.

DETAILED DESCRIPTION

A drop detector for detecting droplets falling into a test tube and generating an audio or visual alarm is described. According to embodiments of present disclosure, as soon as a first drop of the droplets is detected into the test tube, the drop detector is enabled for generating an alert in form of an audio alarm or visual alarm. The test tube may be placed within a Drop Detector casing in order to enable electronic and optical components to work in unison for providing feedback to a doctor about the droplets falling into the test tube, in real time. Further, a detail working of the drop detector is explained in detail in following paragraphs.

General Working Conditions and Setup

Figure 1:
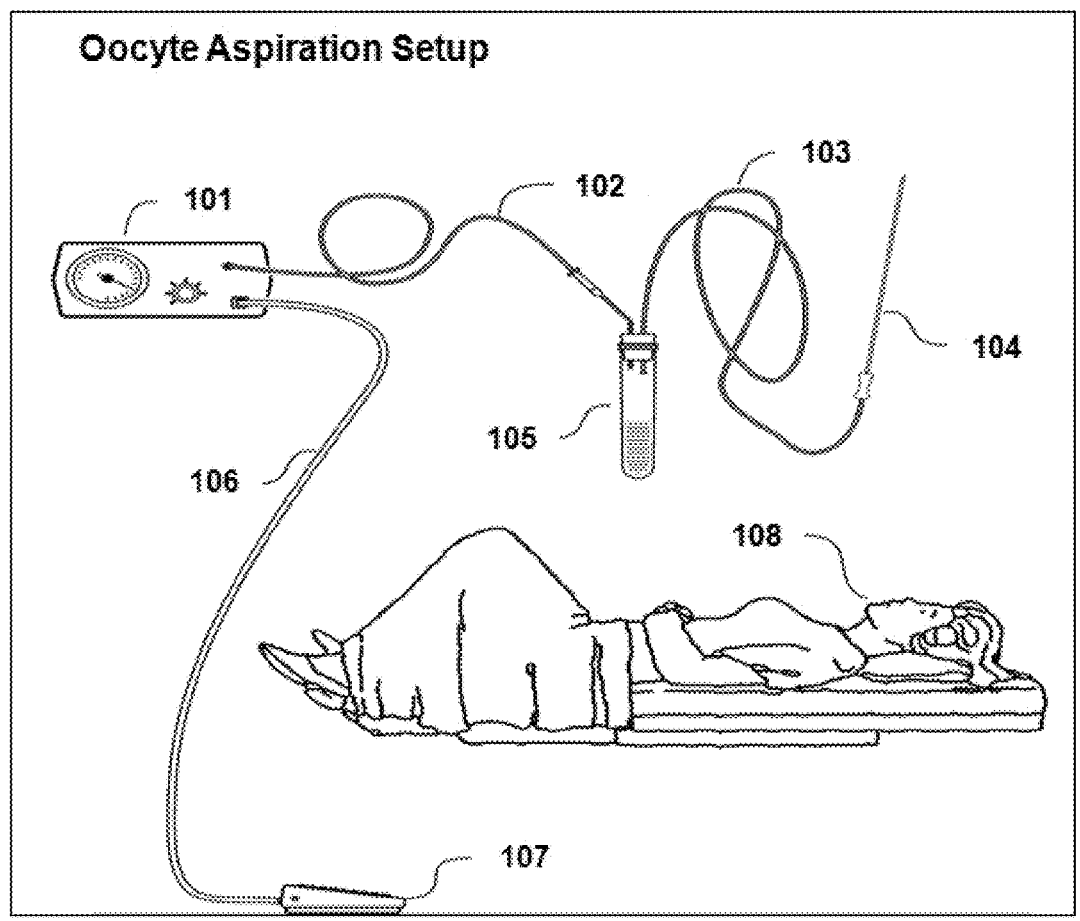
FIG. 1 is an Oocyte aspiration setup illustrating various components used in aspiration process for obtaining one or more oocyte from a female patient.

Referring to FIG. 1, an Oocyte aspiration setup is shown, in accordance with an embodiment of present disclosure. The Oocyte aspiration setup for retrieving an oocyte from a female patient is shown in detail. It may be seen from FIG. 1 that the female patient 108 is on an Operation Theatre (OT) table in a lithotomic position under anesthesia. Further, for performing the oocyte aspiration various components are provided, wherein said components may comprise a vacuum generating unit 101, a suction tube 102, an inlet tube 103, a needle 104, a test tube 105, tube 106, and a foot switch/foot pedal 107.

The vacuum generating unit 101, also known as an aspirator, is a mains power operated device. The aspirator 101 is connected to the test tube 105 by the suction tube 102. The aspirator may be also connected to the foot switch 107, which is placed on the floor for the doctor to operate whenever he/she requires vacuum to be generated in the suction tube 102 which is further connected to the test tube 105.

The other tube i.e., the inlet tube 103 coming out from the test tube 105 is attached to the long needle 104. Further, the needle 104 may be used to insert into the patient till its tip reaches her ovaries, where the oocyte are found suspended in the follicle fluid.

In the general practice, the test tube 105 is held in the hand by a nurse or any other person assisting the doctor during the aspiration. The nurse is supposed to give a feedback to the doctor orally about the droplets flowing status. Thus, during this oral communication there may be a chance of a mismatch or misunderstanding between the nurse and the doctor. Hence, to overcome such situation the present disclosure provides a mechanism for automatically detecting the droplet falling into the test tube 105 and simultaneously notifying the doctor by means of an alarm (audio or visual).

Drop Detector

Figure 2:
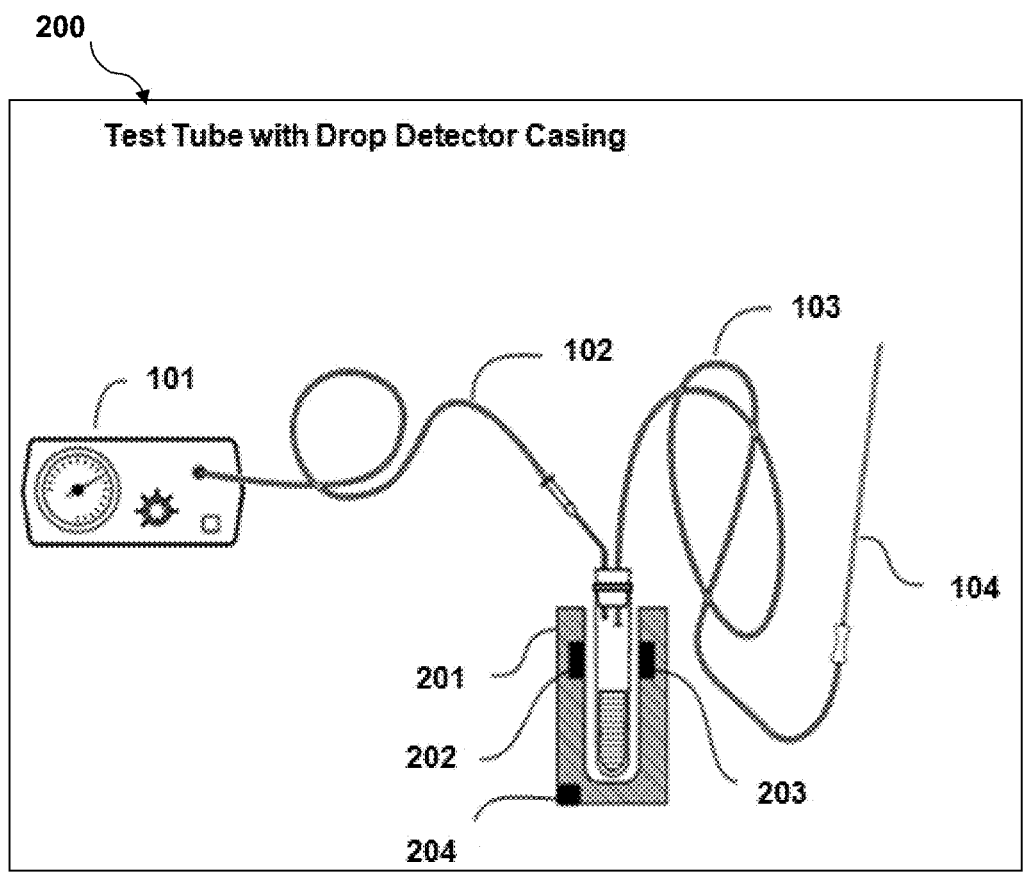
FIG. 2 illustrates an apparatus comprising a Drop Detector Casing and a test tube in which the follicle drops are to be detected.

Referring to FIG. 2, an apparatus 200 comprising an arrangement of a drop detector casing and the test tube is shown, in accordance with an embodiment of present disclosure. The Drop Detector Casing 201 will hold the test tube 105 in its designed cavity appropriately made to measure for the test tube 105. The test tube 105 is placed in the designed cavity in such a manner that it gets aligned with an optical devices i.e., an emitter 202 and detector 203 which are responsible for detecting the drops of the follicle fluid falling into the test tube 105. Further, a signal processing circuitry 204 along with other circuitries i.e., electrical and optical may reside inside the Drop Detector Casing 201. The signal processing circuitry 204 comprises a processor 401 (shown in FIG. 5), wherein the signal processing circuitry 204 may be further coupled with the test tube 105.

Location of Optics Device

Figure 3:
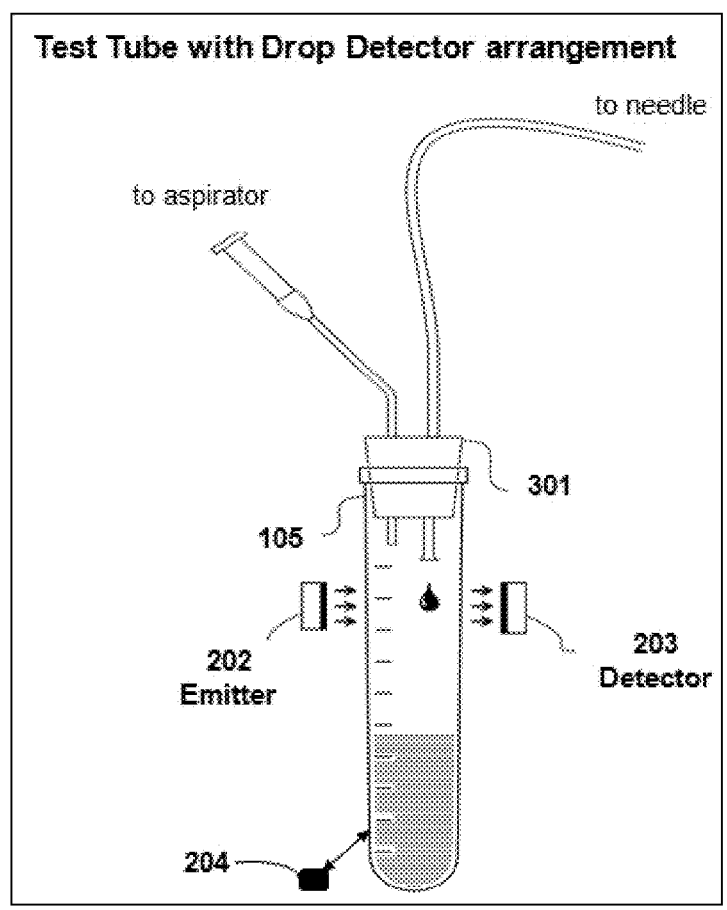
FIG. 3 illustrates an arrangement of optical devices of the Drop Detector casing along with the test tube.

Referring to FIG. 3, illustrates an arrangement of a pair of optical devices with the drop detector casing, in accordance with an embodiment of present disclosure. The optical devices comprise an emitter 202 and a detector 203. In one embodiment, the emitter 202 may be an infra-red (IR) light emitting diode and the detector 203 may be infra-red (IR) detector. The optical devices (202 and 203) are placed on opposite side of the test tube 105, wherein the opposite side refers to a position where the incoming fluid flow breaks into a drop and detaches from the end-point of the inlet tube 103 inside the test tube 105, before falling into the collected fluid in the test tube 105.

Figure 4:
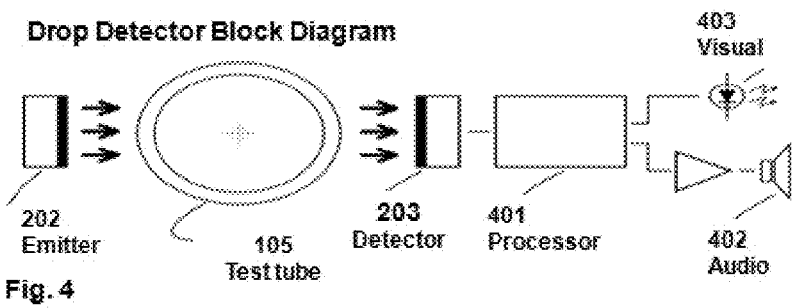
FIG. 4 illustrates a functional block diagram of a Drop Detector.

Referring to FIG. 4, a functional block diagram of the drop detector is shown, in accordance with an embodiment of present disclosure. The drop detector comprises the emitter 202, the detector 203, a processor 401 of the signal processing circuitry 204, an audio indicator 402, and a visual indicator 403. The detail description of the drop detector is explained by referring to FIG. 5 as below.

Figure 5:
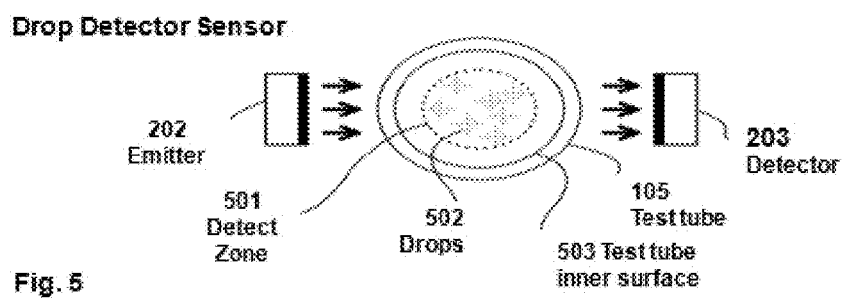
FIG. 5 illustrates a drop detect sensor for detecting droplets in the test tube in accordance with one embodiment of the present disclosure.

Referring now to FIG. 5, a drop detect sensor in shown, in accordance with an embodiment of present disclosure. As mentioned above, the optical devices i.e., the emitter 202 and the detector 203 are placed on the opposite side of the test tube 105. The falling drop location cannot be ascertained to a defined spot. Thus, to detect the drops, a detect zone 501, also referred as an expected zone, may be defined within which every drop may fall. Further, the detect zone 501 is about 6 to 7 mm in diameter which is slightly smaller than the inner wall 503 of the test tube 105. The detect zone 501 is a result of the inlet tube 103 being at off centre of the cork with no fixed location for it to be placed onto. So each time someone places it on the test tube 105 its position can lie anywhere within the detect zone 501. As long as the test tube 105 is positioned vertically and not shaken, the falling drop will always pass through the detect zone 501.

For detecting the first and the subsequent drops of the follicle fluid in the detect zone, the signal processing circuitry 204 (comprising the processor 401) coupled with the test tube 105, monitors the intensity of the beam of light received by the detector 203. Further, the signal processing circuitry 204 may compare the intensity of the beam of light with a pre-defined intensity. In one aspect, the pre-defined intensity indicates the intensity of light emitted by the first optical device 202. Based on the comparison, if a difference between the pre-defined intensity and intensity is determined to be greater than a pre-defined threshold value, the signal processing circuitry 204 generates a valid electrical signal indicating the detection of the first drop of the follicle fluid falling into the test tube 105. Similarly, the subsequent drops of the follicle fluid may be detected by the signal processing circuitry 204 by comparing the intensity of the beam of light with the pre-defined intensity each time when the subsequent drops passes through the detect zone. The functioning of the signal processing circuitry 204 may be understood with following example. Considering a case where the pre-defined intensity is 100 units, the intensity received, by the second optical device, is 80 units, and the pre-defined threshold value is 15. Now in order to detect the first and the subsequent drops of the follicle fluid, the signal processing circuitry 204 calculates the difference between the pre-defined intensity and the intensity received by the second optical device (i.e. 100−80).

Upon calculating, it may be understood that the difference is 100–80 units=20 units. Since the predefined threshold value set for the difference is 15 units (i.e. beam to be received by the second optical device 203 should not deviate by more than 15 units), therefore in this case the first drop is detected by the signal processing circuitry 204.

Figure 7:
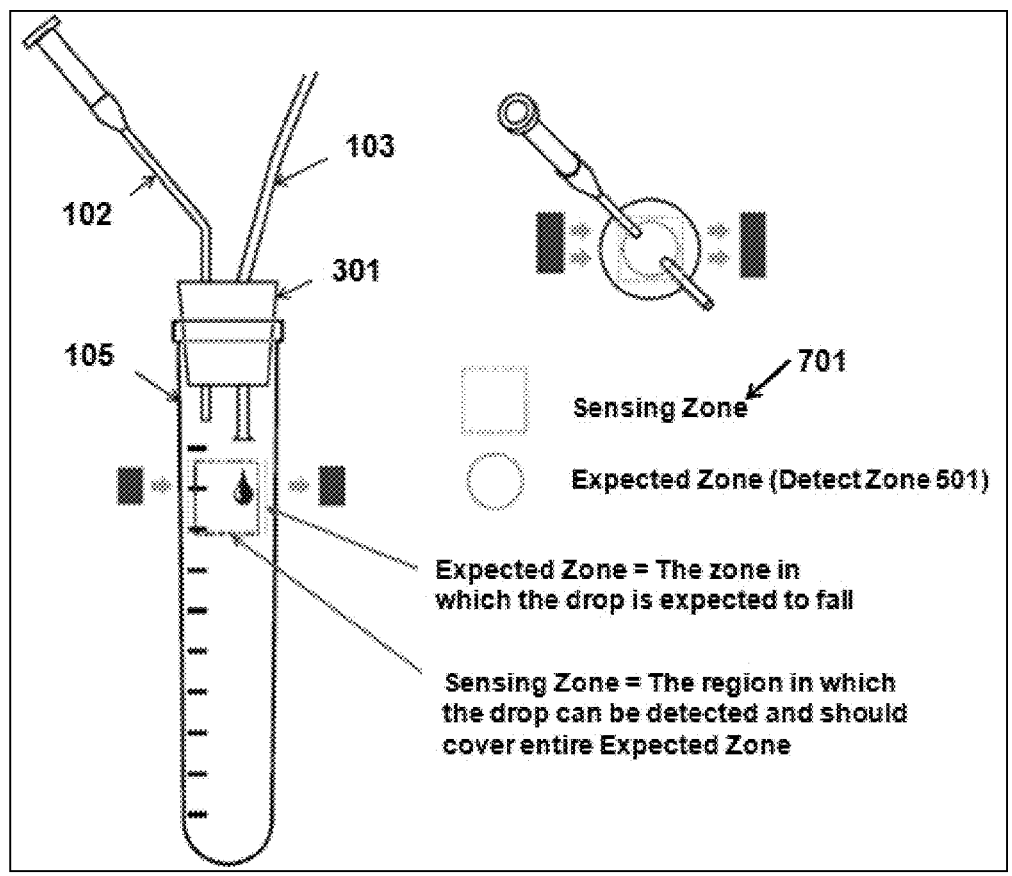
FIG. 7 illustrates detail explanation of a detect zone (i.e., expected zone) and a sensing zone for detecting the droplets.

Further, the valid electrical signal (generated by the signal processing circuitry 204) may be used to initiate the audio indicator 402 and visual indicator 403 for generating an alarm. Thus, alarm may notify the doctor (or any user using the apparatus) about the timely retrieval of the follicle fluid in the test tube 105. According to embodiment of present disclosure, a sensing zone 701 as illustrated in FIG. 7 may be defined between the detect zone 501 and the inner wall 503 of the test tube 105. The purpose of defining the sensing zone 701 is to ensure that no droplet passes undetected while falling into the test tube 105. Since, the inlet tube 103 coming out from the needle 104 is not placed at the centre of a stopper, it may be required to define a zone for detecting the droplets falling into the test tube 105. When a nurse presses the stopper on the test tube 105 the position of falling droplets depends upon the stopper position. Since, the position of the stopper is never aligned there may be a deviation in the test tube where the droplets may be expected to fall. Thus, to overcome such scenario, an additional layer of zone may be defined i.e., the sensing zone 701. For example, assuming the inlet tube 103 is 3 mm off the axis which will give 6 mm circular zone as the expected zone i.e., the detect zone 501. Further, for providing safety margin of 0.5 mm at the radius, the sensing zone 701 may be defined which may be equal to 7 mm.

Figure 6:
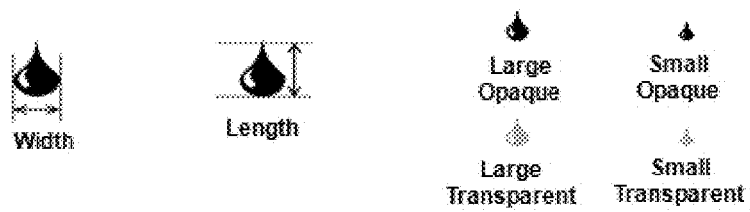
FIG. 6 illustrates follicle fluid droplets of variable sizes and different colors that may be detected using the drop detector, in accordance with one embodiment of the present disclosure.

Referring now to FIG. 6, a follicle fluid of different dimensions and colors is shown, in accordance with an embodiment of present disclosure. The follicle fluid retrieved from a patient may vary in its color and opacity, depending on several factors. The follicle fluid may be very light in color and almost transparent like light yellow colored water or may contain a large amount of blood, making it appear almost like the blood, dark and opaque. According to embodiments of present disclosure, the follicle fluid drop may vary in its width or diameter from 1.2 mm to 2.6 mm, whereas its length may vary from range of 2 mm to 4 mm. The optical and electronic circuitry combined together makes it possible to detect each and every drop falling into the test tube 105 irrespective of its size or optical characteristics. Thus, the fluid droplets of all sizes and colors may be detected without having to adjust or tune any part, mechanical, optical or electrical component of the drop detection device.

Figure 8:
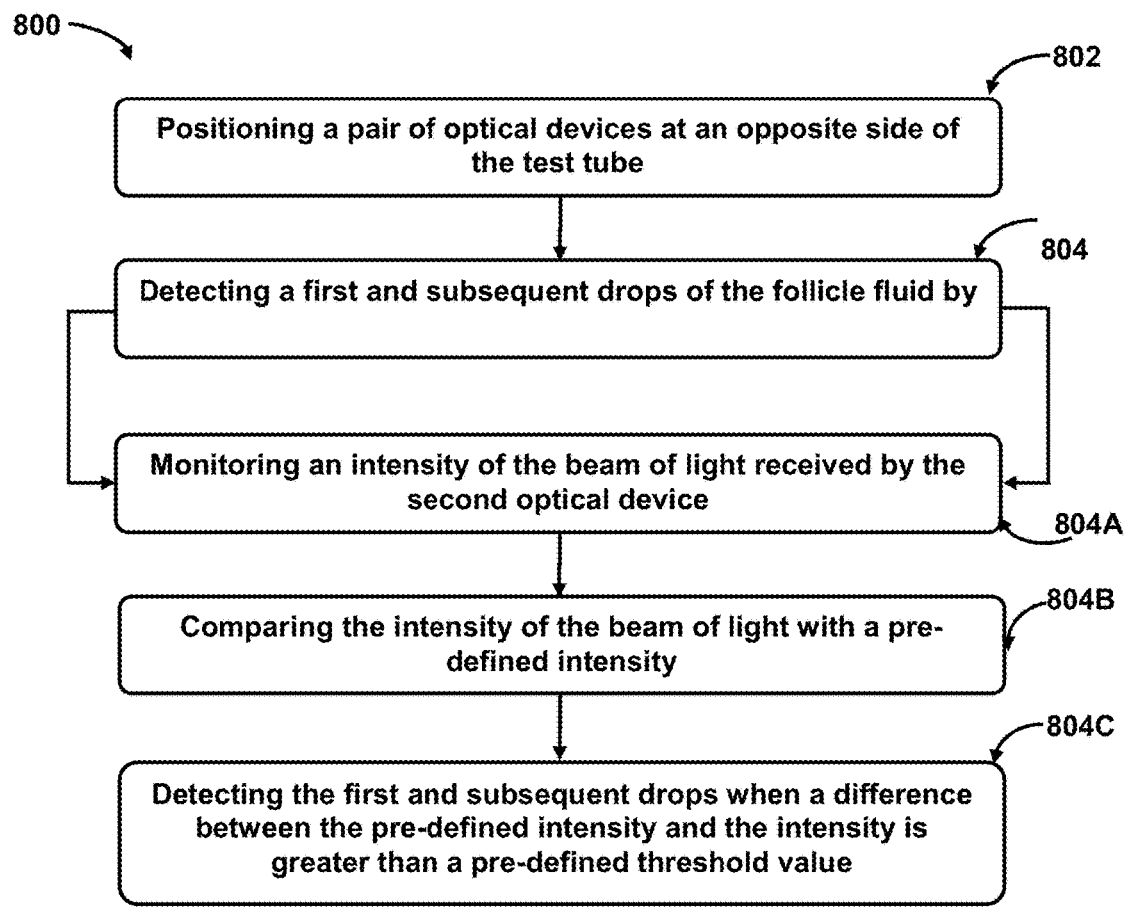
FIG. 8 illustrates a method for detecting a drop of follicle fluid falling into a test tube, in accordance with an embodiment of the present disclosure.

Referring now to FIG. 8, method for detecting a drop of follicle fluid falling into a test tube is shown, in accordance with an embodiment of the present disclosure. The order in which the method 800 is described is not intended to be construed as a limitation, and any number of the described method blocks can be combined in any order to implement the method 800 or alternate methods. Additionally, individual blocks may be deleted from the method 800 without departing from the spirit and scope of the disclosure described herein. However, for ease of explanation, in the embodiments described below, the method 800 may be considered to be implemented in the above described apparatus 200.

At block 802, a pair of optical devices is positioned at an opposite side of the test tube 105. The test tube 105 has a cork fitted at open-end of the test tube 105, wherein the cork has a passage allowing an inlet tube 103, carrying the follicle fluid, to pass through the test tube 105. Further, the opposite side indicates a position on the test tube 105 where an incoming follicle fluid flow breaks into a drop and detaches from the inlet tube 103. Further, the pair of the optical devices comprises a first optical device and a second optical device. The first optical device emits a beam of light, through the test tube 105, towards the second optical device.

At block 804, the first and subsequent drops of the follicle fluid may be detected by performing the steps shown in the blocks 804A-804C.

At block 804A, an intensity of the beam of light received by the second optical device is monitored.

At block 804B, the intensity of the beam of light is compared with a pre-defined intensity.

At block 804C, the first and subsequent drops of the follicle fluid in the test tube 105 is detected when a difference between the pre-defined intensity and the intensity is determined to be greater than a pre-defined threshold value.

Although implementations for method and apparatus for detecting drops of the follicle fluid have been described in language specific to structural features and/or methods, it is to be understood that the appended claims are not necessarily limited to the specific features or methods described. Rather, the specific features and methods are disclosed as examples of implementations for detecting the drops of the follicle fluid falling into the test tube and notifying the user about the timely retrieval/extraction of the follicle fluid from the patient's body.

We claim:

1. An apparatus for detecting a drop of follicle fluid falling into a test tube, the apparatus comprising:
   a test tube for storing follicle fluid, wherein the test tube has a cork fitted at open-end of the test tube, and wherein the cork has a passage allowing an inlet tube, carrying the follicle fluid, to pass through the test tube;
   a pair of optical devices positioned at an opposite side of the test tube,
   wherein the opposite side indicates a position on the test tube where an incoming follicle fluid flow breaks into a drop and detaches from the inlet tube, and wherein the pair of the optical devices comprises a first optical device and a second optical device, and wherein the first optical device emits a beam of light of a pre-defined intensity, through the test tube, towards the second optical device;
   a signal processing circuitry, coupled with the test tube, to detect first and subsequent drops of the follicle fluid by monitoring an intensity of the beam of light received by the second optical device, comparing the intensity of the beam of light with the pre-defined intensity, and detecting the first and subsequent drops of the follicle fluid in the test tube based upon a difference between the pre-defined intensity and the intensity being determined as greater than a pre-defined intensity threshold value; and
   wherein the apparatus further comprises an alert mechanism for generating an audio alert and a visual alert for indicating to an operator that the first and subsequent drops of the follicle fluid are falling into the test tube.

2. The apparatus of claim 1, wherein the first optical device is an emitter and the second optical device is a detector.

3. The apparatus of claim 1, wherein the difference is based on opacity or transparency properties of the follicle fluid.

4. A method for detecting a drop of follicle fluid falling into a test tube, the method comprising:

positioning a pair of optical devices at an opposite side of the test tube, wherein the test tube has a cork fitted at open-end of the test tube, and wherein the cork has a passage allowing an inlet tube, carrying the follicle fluid, to pass through the test tube, and wherein the opposite side indicates a position on the test tube where an incoming follicle fluid flow breaks into a drop and detaches from the inlet tube, and wherein the pair of the optical devices comprises a first optical device and a second optical device, and wherein the first optical device emits a beam of light of a pre-defined intensity, through the test tube, towards the second optical device; and detecting, by a signal processing circuitry coupled with the test tube, first and subsequent drops of the follicle fluid by monitoring an intensity of the beam of light received by the second optical device, comparing the intensity of the beam of light with the pre-defined intensity, and detecting the first and subsequent drops of the follicle fluid in the test tube based upon a difference between the pre-defined intensity and the intensity being determined as greater than a pre-defined intensity threshold value; and wherein the method further comprises generating an audio alert and a video alert, by an alert mechanism, for indicating to an operator that the first and subsequent drops of the follicle fluid are falling into the test tube.

5. The method of claim 4, wherein the first optical device is an emitter and the second optical device is a detector.

6. The method of claim 4, wherein the difference is based on opacity or transparency properties of the follicle fluid.

* * * * *